United States Patent
Kummerfeld et al.

(10) Patent No.: US 9,314,603 B2
(45) Date of Patent: Apr. 19, 2016

(54) DEVICE FOR DISINFECTING WOUND TREATMENT

(71) Applicant: Dräger Medical GmbH, Lübeck (DE)

(72) Inventors: Ryszard Kummerfeld, Travemünde (DE); Hans-Ullrich Hansmann, Barnitz (DE); Hanno Kretschmann, Hamburg (DE)

(73) Assignee: Dräger Medical GmbH, Lübeck (DE)

( * ) Notice: Subject to any disclaimer, the term of this patent is extended or adjusted under 35 U.S.C. 154(b) by 39 days.

(21) Appl. No.: 13/774,255

(22) Filed: Feb. 22, 2013

(65) Prior Publication Data

US 2013/0226073 A1    Aug. 29, 2013

(30) Foreign Application Priority Data

Feb. 23, 2012    (DE) .................. 10 2012 003 563

(51) Int. Cl.
| | |
|---|---|
| *H05H 1/34* | (2006.01) |
| *A61M 37/00* | (2006.01) |
| *A61L 2/14* | (2006.01) |

(52) U.S. Cl.
CPC ........ *A61M 37/00* (2013.01); *A61L 2/14* (2013.01); *A61L 2202/14* (2013.01)

(58) Field of Classification Search
CPC ... H05H 1/34; H05H 1/24; H05H 2001/3468; H05H 2245/122; A61B 18/042; A61L 2/14
USPC .............. 604/20, 24; 606/40, 41, 43
See application file for complete search history.

(56) References Cited

U.S. PATENT DOCUMENTS

| | | | | |
|---|---|---|---|---|
| 3,026,874 A | * | 3/1962 | Stevens .................. | 604/305 |
| 3,649,805 A | * | 3/1972 | Rohrberg ................ | 219/121.5 |
| 3,707,615 A | * | 12/1972 | Rotolico et al. ......... | 219/121.47 |
| 3,803,380 A | * | 4/1974 | Ragaller ................. | 219/121.47 |
| 4,265,747 A | * | 5/1981 | Copa et al. ............. | 210/758 |
| 4,559,671 A | * | 12/1985 | Andrews et al. ........ | 16/421 |
| 4,647,295 A | * | 3/1987 | Christ .................... | 95/284 |
| 4,781,175 A | * | 11/1988 | McGreevy et al. ...... | 606/40 |
| 4,877,937 A | * | 10/1989 | Muller ................... | 219/121.59 |
| 5,014,389 A | * | 5/1991 | Ogilvie et al. .......... | 15/353 |
| 5,278,387 A | * | 1/1994 | Borne ................... | 219/121.39 |
| 5,328,516 A | * | 7/1994 | Dietiker ................ | 118/723 DC |
| 5,437,651 A | * | 8/1995 | Todd et al. ............ | 604/313 |
| 5,548,611 A | * | 8/1996 | Cusick et al. .......... | 373/18 |

(Continued)

FOREIGN PATENT DOCUMENTS

| | | | |
|---|---|---|---|
| CN | 1 372 976 A | 10/2002 | |
| CN | 1 781 462 A | 6/2006 | |

(Continued)

*Primary Examiner* — Scott Medway
(74) *Attorney, Agent, or Firm* — McGlew and Tuttle, P.C.

(57) ABSTRACT

A device (10) for disinfecting wound treatment is described, with a housing (18), with a plasma generator (54) arranged in housing (18) for generating a disinfecting plasma, with a flow module (52) arranged in housing (18) for generating a gas stream, which forms a free jet (32) transporting the disinfecting plasma from housing (18), and with a jet control unit (50) for affecting the free jet (32) in a planned manner by controlling the gas stream generated by flow module (52). Means (10) has, furthermore, a guide apparatus (56) controllable via the jet control unit (50) for guiding the free jet (32).

19 Claims, 7 Drawing Sheets

(56) References Cited

U.S. PATENT DOCUMENTS

| | | | |
|---|---|---|---|
| 5,843,079 A * | 12/1998 | Suslov | 606/43 |
| 5,916,465 A * | 6/1999 | New et al. | 219/138 |
| 6,013,075 A * | 1/2000 | Avramenko et al. | 606/40 |
| 6,114,649 A * | 9/2000 | Delcea | 219/121.52 |
| 6,206,878 B1 * | 3/2001 | Bishop et al. | 606/49 |
| 6,262,386 B1 * | 7/2001 | Fornsel | 219/121.52 |
| 6,335,595 B1 * | 1/2002 | Nishikawa et al. | 315/111.21 |
| 6,429,400 B1 * | 8/2002 | Sawada et al. | 219/121.52 |
| 6,448,565 B1 * | 9/2002 | Erath | 250/423 R |
| 6,475,215 B1 * | 11/2002 | Tanrisever | 606/45 |
| 6,629,974 B2 * | 10/2003 | Penny et al. | 606/41 |
| 6,676,802 B2 * | 1/2004 | Roth | 156/345.35 |
| 6,774,336 B2 * | 8/2004 | Horner-Richardson et al. | 219/121.51 |
| 6,780,184 B2 * | 8/2004 | Tanrisever | 606/45 |
| 6,800,336 B1 * | 10/2004 | Fornsel et al. | 427/562 |
| 6,920,312 B1 * | 7/2005 | Benjamin | 455/69 |
| 6,958,063 B1 * | 10/2005 | Soll et al. | 606/41 |
| 6,989,505 B2 * | 1/2006 | MacKenzie et al. | 219/121.53 |
| 7,300,436 B2 * | 11/2007 | Penny et al. | 606/34 |
| 7,338,482 B2 * | 3/2008 | Lockwood et al. | 604/543 |
| 7,589,473 B2 * | 9/2009 | Suslov | 315/111.21 |
| 7,601,150 B2 * | 10/2009 | Farin | 606/40 |
| 7,608,839 B2 * | 10/2009 | Coulombe et al. | 250/426 |
| 7,785,322 B2 * | 8/2010 | Penny et al. | 606/34 |
| 7,862,564 B2 * | 1/2011 | Goble | 606/41 |
| 7,875,356 B2 * | 1/2011 | Hilmer et al. | 428/425.5 |
| 7,921,804 B2 * | 4/2011 | Lee | 118/723 MW |
| 7,928,338 B2 * | 4/2011 | Suslov | 219/121.47 |
| 8,316,172 B2 * | 11/2012 | Gainey et al. | 710/260 |
| 8,338,806 B2 * | 12/2012 | Graf et al. | 250/492.3 |
| 8,614,404 B2 * | 12/2013 | Twarog et al. | 219/121.44 |
| 2001/0034519 A1 * | 10/2001 | Goble et al. | 606/41 |
| 2003/0108460 A1 * | 6/2003 | Andreev et al. | 422/186.07 |
| 2003/0125727 A1 * | 7/2003 | Truckai et al. | 606/41 |
| 2004/0122434 A1 * | 6/2004 | Argenta et al. | 606/86 |
| 2004/0147501 A1 * | 7/2004 | Dolmans et al. | 514/185 |
| 2005/0187542 A1 * | 8/2005 | Auge et al. | 606/32 |
| 2005/0256519 A1 * | 11/2005 | Goble et al. | 606/34 |
| 2005/0274122 A1 * | 12/2005 | Chang et al. | 62/5 |
| 2006/0037947 A1 * | 2/2006 | Schneider | 219/121.48 |
| 2006/0116669 A1 * | 6/2006 | Dolleris | 606/17 |
| 2007/0062332 A1 * | 3/2007 | Jones et al. | 75/338 |
| 2007/0212254 A1 * | 9/2007 | Nagatsu | 422/21 |
| 2007/0260230 A1 * | 11/2007 | Youngquist et al. | 606/9 |
| 2007/0284340 A1 * | 12/2007 | Jorgensen | 219/121.5 |
| 2008/0091187 A1 * | 4/2008 | Ferren et al. | 606/36 |
| 2008/0185366 A1 * | 8/2008 | Suslov | 219/121.47 |
| 2008/0237484 A1 * | 10/2008 | Morfill et al. | 250/427 |
| 2009/0047439 A1 * | 2/2009 | Withers et al. | 427/448 |
| 2011/0220143 A1 * | 9/2011 | Buske et al. | 134/1.1 |
| 2012/0046597 A1 * | 2/2012 | Morfill et al. | 604/20 |
| 2012/0172789 A1 * | 7/2012 | Fischer et al. | 604/24 |
| 2012/0296261 A1 * | 11/2012 | Whitaker et al. | 604/20 |
| 2013/0082034 A1 * | 4/2013 | Foret | 219/121.52 |
| 2013/0199540 A1 | 8/2013 | Buske | |
| 2013/0319460 A1 * | 12/2013 | Schneider et al. | 134/1.1 |

FOREIGN PATENT DOCUMENTS

| | | |
|---|---|---|
| DE | 10 2009 028190 A1 | 2/2011 |
| DE | 10 2010 011 643 A1 | 9/2011 |

* cited by examiner

DEVICE FOR DISINFECTING WOUND TREATMENT

CROSS REFERENCE TO RELATED APPLICATIONS

This application claims the benefit of priority under 35 U.S.C. §119 of German Patent Application 10 2012 003 563.2 filed Feb. 23, 2012, the entire contents of which are incorporated herein by reference.

FIELD OF THE INVENTION

The present invention pertains to a device for disinfecting wound treatment, with a housing, with a plasma generator arranged in the housing for generating a disinfecting plasma, with a flow module arranged in the housing for generating a gas stream, which forms a free jet transporting the disinfecting plasma from the housing, and with a jet control unit for affecting the free jet in a planned manner by controlling the gas stream generated by the flow module.

BACKGROUND OF THE INVENTION

Disinfecting wound treatment for avoiding infection of the patient due to entry of microorganisms into the surgical wound is of the highest priority in an operating room. Open wounds, which occur, for example, in case of severe bone fractures, represent a great challenge in terms of hygiene, especially against the background of the increase in multi resistant bacteria, which have been a major problem in medical facilities for a long time.

A great variety of measures, e.g., the disinfection of medical devices with the use of disinfectants, sterilization of medical instruments with sterilizing devices intended specifically for this purpose, or even administration of antibiotics at comparatively high doses, have been used to avoid an infection of a patient. Since stressful, lengthy and cost-intensive after treatment are necessary in case of an infection, there is an urgent need for simple and cost-effective measures for disinfecting wound treatment.

Attempts have been made in the recent past to also utilize the sterilizing effect of plasma for medical purposes. One example of this can be found in DE 10 2009 028 190 A1. A hand-held plasma device, which operates with a so-called cold, HF-excited plasma under atmospheric pressure conditions, is disclosed there. The plasma is generated by a plasma generator arranged in the housing of the device and is transported from the housing of the device in a gas stream in the form of a free jet. The orientation and expansion of the free jet leaving the housing of the device are set in this device by the special design of the discharge nozzle used therefor. A simple guiding of the free jet, for example, by varying the expansion of the jet and/or the direction in which the jet is discharged, is not possible with this device.

SUMMARY OF THE INVENTION

An object of the present invention is to improve a device of the type mentioned in the introduction such that it makes possible a simple and reliable wound treatment in an operating room.

According to the invention, a device is provided for disinfecting wound treatment. The device comprises a housing, a plasma generator arranged in the housing for generating a disinfecting plasma, a flow module arranged in the housing for generating a gas stream, which forms a free jet transporting the disinfecting plasma from the housing, and a guide apparatus for guiding the free jet and a jet control unit. The jet control unit controls the guide apparatus for affecting the free jet in a planned manner by controlling the gas stream generated by the flow module.

The present invention provides the guiding apparatus such that it is controllable by means of a jet control unit for guiding the free jet. It is possible as a result to control the free jet such that it is guided to the wound to be disinfected in a desired manner. The "free jet" will be defined below as the gas stream being discharged from the housing into the free environment, whereas the term "guide" is defined as any way of affecting the distribution of the free jet in space, especially the expansion and direction of discharge thereof.

The gas stream transporting the disinfecting plasma can be set by the guiding of the free jet, which is possible by means of the controllable guiding apparatus, such that the plasma acts in a locally limited area only, namely, the wound area to be treated. This local limitations of the plasma activity is used especially to protect the surgical staff, which would be exposed to a non-tolerable long-term burden in case of distribution of the plasma in a wide space.

It is apparent that the device according to the present invention can be used not only to disinfect the wound area, but for other work areas as well. For example, it is possible to disinfect operating tables or wound treatment kits by means of the device.

The gas stream, which transports the disinfecting plasma from the housing, may be obtained from the room air in an especially simple embodiment. However, it is also possible to use other gases, e.g., argon, as the transport medium.

The plasma generator, which generates the plasma added to the gas stream in the disinfecting device according to the present invention, operates in a known manner per se. For example, it is thus possible to generate the plasma by means of nanostructured surfaces. The plasma is preferably generated as a so-called cold plasma under atmospheric pressure conditions. The ionized gas molecules forming the plasma have, for example, a life in the range of about 20 sec. During this life, they have the property of destroying simple cells such as bacteria without causing significant damage to more highly developed cells.

In an advantageous variant, the jet control unit controls the guide apparatus to vary the jet cross section and/or the direction of discharge of the free jet leaving the housing. Wound treatment is made considerably more simple for the surgical staff especially by the variation of the jet cross section, which is made possible with the guide apparatus. It is thus possible, for example, to set the jet cross section of the free jet by means of the guide apparatus as a function of the distance from the wound area to be treated such that the area to be disinfected with the plasma has the desired size.

In an especially preferred embodiment, the guide apparatus has at least one guide element, which is arranged at a gas discharge opening of the housing and can be positioned variably. The guide element arranged at the gas discharge opening is, for example, a guide plate that can be arranged at variable angles, which makes it possible to shape the gas stream forming the free jet as desired. It is also possible to arrange a plurality of guide plates, which can be oriented in relation to one another as desired in order to affect the free jet in the desired manner. The guide plates may be shaped, for example, parabolically for this. Also conceivable is an arrangement in which a movable first guide element is moved in relation to a stationary second guide element. The stationary guide element is formed, for example, from a ring, while the movable guide element is designed as a cone, which is arranged in the area of the ring opening and is adjustable in relation to the ring in the direction in which the gas stream expands in order to shape the gas stream in the desired manner.

The jet control unit preferably controls the flow module such that the velocity of the gas stream is set at a desired value. This desired value is usually set such that the free jet generated by the gas stream outside the housing has a velocity that is, on the one hand, so low that the plasma being transported with the free jet is present in the region of the wound area during a sufficiently long residence time to exert disinfecting action there. On the other hand, it should be so high that the free jet can be guided through the guide apparatus in the desired manner and thus reaches the wound area with the desired jet shape in the first place. When assuming, merely by way of an example, a working distance of 1 m, the velocity at which the gas stream is discharged from the housing of the disinfection device according to the present invention might be, in terms of an order of magnitude, in a range of about 20 cm/sec.

Consequently, the actuation of the flow module in the above-described sense offers the surgical staff the possibility of optimizing the velocity of the free jet, i.e., to minimize it, as a rule, to the extent as this is possible in the particular application under the secondary condition of the desired ability to shape the jet. Such minimization of the free jet velocity is favorable for wound healing because, for example, the wound is prevented from drying out.

The jet control unit advantageously controls the plasma generator such that the desired plasma concentration is set in the gas stream. Consequently, in this embodiment the jet control unit affects not only the spread of the free jet, i.e., especially the velocity thereof, jet cross section and direction of discharge, but also the plasma concentration in the jet. The disinfection device according to the present invention can thus be handled in an even more simple manner.

In an especially preferred embodiment, the jet control unit has at least one sensor for detecting an actuating variable and controls the gas stream as a function of this actuating variable. Any variable that could affect how the free jet can be set in an advantageous manner in the concrete application, e.g., in respect to the plasma concentration, jet velocity, jet cross section, jet discharge direction, etc., may be used as an actuating variable. The sensor, which detects such an actuating variable, makes possible the automatic control of the above-mentioned parameters for optimally adapting the free jet to the particular application, without the surgical staff having to do anything for this.

The sensor is, for example, an ozone sensor, which detects the ozone concentration in the ambient air as an actuating variable. Ozone is usually formed from the oxygen of the air during plasma generation, and even though it has a disinfecting action like the radicals present in the plasma and is thus definitely desirable, it does represent a health hazard for the surgical staff beginning from a certain concentration. If, for example, the ozone sensor detects that the ozone concentration exceeds a tolerable value, the jet control unit could put the plasma module automatically out of operation in order to prevent the ozone concentration from rising further. It is also conceivable, for example, to detect the ozone concentration in the region of the wound area in question. The ozone concentration could then be inferred from the ozone concentration detected and the plasma generator could be actuated correspondingly to increase or decrease the plasma generation.

In an especially preferred embodiment, the sensor is a distance sensor, which detects the distance between the device and a wound area to be treated as an actuating variable. Depending on the detected working distance, the jet cross section and hence the expansion of the free jet directed towards the wound area can be varied, for example, in this case. Since the free jet expands with increasing path length in the space, it is conceivable, for example, to reduce the jet cross section with increasing working distance in order for the surface area of the wound area that is exposed to the free jet to remain nearly constant independently from the working distance.

The use of a distance sensor also makes it possible to optimally adapt the plasma concentration to the working distance. The quantities of plasma generated can thus be minimized in order to save energy and costs and to protect the surgical staff from any possible harmful effects of the plasma.

The free jet can also be affected in another way depending on the working distance detected by the sensor. For example, the velocity at which the flow module ejects the gas stream can thus be set as a function of the distance. The greater the working distance, the higher could be, for example, the value at which the velocity of the gas stream is set in order to ensure that the plasma contained in the gas stream will reach the wound area to be treated.

For example, an optical sensor, which detects the travel time of a signal sent out by it and reflected at the wound area and determines the working distance herefrom, can be used as a distance sensor. However, the working distance may also be detected in another manner, e.g., capacitively or inductively. The disinfection device may also be equipped with a camera, which detects the working distance, for example, by means of an autofocus optical system. The use of an acoustic distance sensor is likewise possible.

A light pointer, which can be controlled by means of the jet control unit and generates a light pattern on the wound area, is preferably provided, the light pattern representing a target area, in which the concentration of the plasma being transported in the free jet is equal to or greater than a desired minimum effective concentration. In an especially preferred embodiment, the light pointer generates the light pattern on the wound area as a function of the actuating variable generated by the sensor, especially as a function of the working distance. Based on the light pattern, the surgical staff can recognize the target area on the wound area within which the plasma concentration is so high that the desired disinfecting action is achieved.

The light pointer may also be, for example, a laser light source such as a laser pointer, which generates the light pattern via a moving laser beam. In this case the laser light beam draws, for example, a circular line, which encloses the target area. The light pattern may, of course, also be generated in another form, e.g., as crosshairs.

The light pointer can be preferably controlled such that the light pattern generated by it on the wound area has an inner area representing the target area and an outer area, which surrounds the inner area and can be visually distinguished from the inner area and represents an area in which the plasma concentration is lower than the minimum effective concentration and higher than a tolerable working concentration. The working concentration preferably now defines a limit beginning from which the plasma concentration is hazardous to the health of the surgical staff, at least over a longer time.

The flow module comprises, for example, a blower, which directs the gas stream towards the plasma generator. The blower draws, for example, ambient air into the housing in this case, and the air stream thus generated is then partially ionized in the housing by the plasma generator. The ionized part of the gas stream forms the plasma having disinfecting action, which is guided in the form of the free jet towards the wound area.

Instead of a blower, a flow module of another type, e.g., a compressed air generator operating according to the ejector principle or a so-called jet stream generator may be used as well.

A movable ceiling suspension, on which the housing is arranged, is used in a preferred embodiment. The disinfection device can be positioned comfortably at the desired distance above the wound area with such a ceiling suspension in order to direct the free jet exactly onto the wound to be disinfected.

A handle, with which the housing can be moved manually, is preferably arranged on the housing. In an especially preferred embodiment, the handle is part of the jet control device and can be actuated manually for controlling the gas stream. It is conceivable, for example, to set the velocity or expansion of the free jet with the handle. The handle forms for this, for example, a bar-shaped element, which is rotatable about its longitudinal axis for controlling the gas stream.

If a sterile cover is provided, which is adapted to the handle and is replaced with a new cover after use, contamination of the disinfection device with microorganisms is reliably prevented.

In an alternative embodiment, the housing may also be mounted on a robot arm, which makes possible an autonomous positioning of the device by means of suitable sensors and actuators.

At least one supply line, which is integrated in the ceiling suspension and leads into the housing, is preferably provided. Via such a supply line, the device can be connected, for example, to a medical gas supply system. Power supply or data transmission is also possible via such a supply line.

In a preferred embodiment, a display device for displaying the operating state is provided. The display device may be used, for example, to inform the surgical staff on whether the plasma module is activated or not at a given point in time. In an embodiment mentioned merely as an example, the display device is a light source, which is arranged at the housing and is put into operation only when the plasma generator is activated. In addition or as an alternative, an acoustic signal transmitter may be provided as well. The display device may also be used to display other operating parameters, e.g., to display the working distance, ozone concentration, free jet velocity, plasma dose, action time, etc.

Provisions are made in an especially preferred embodiment for an apron provided with an opening for the wound for locally limiting the plasma in the region of a wound area. The apron is placed on the patient such that the wound to be treated is exposed through the opening for the wound, whereas the areas surrounding the wound are protected by the apron from the effect of the plasma.

The apron is formed, for example, from a ring-shaped tube, which has a plurality of suction openings and a suction pipe connection for connecting a suction device. If the suction device is put into operation, the gas cloud containing the plasma is drawn via the suction openings into the tube and thus removed from the wound area. The exhausted gas can then be filtered, for example, by means of activated carbon and rendered harmless.

The present invention will be explained below on the basis of an exemplary embodiment with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
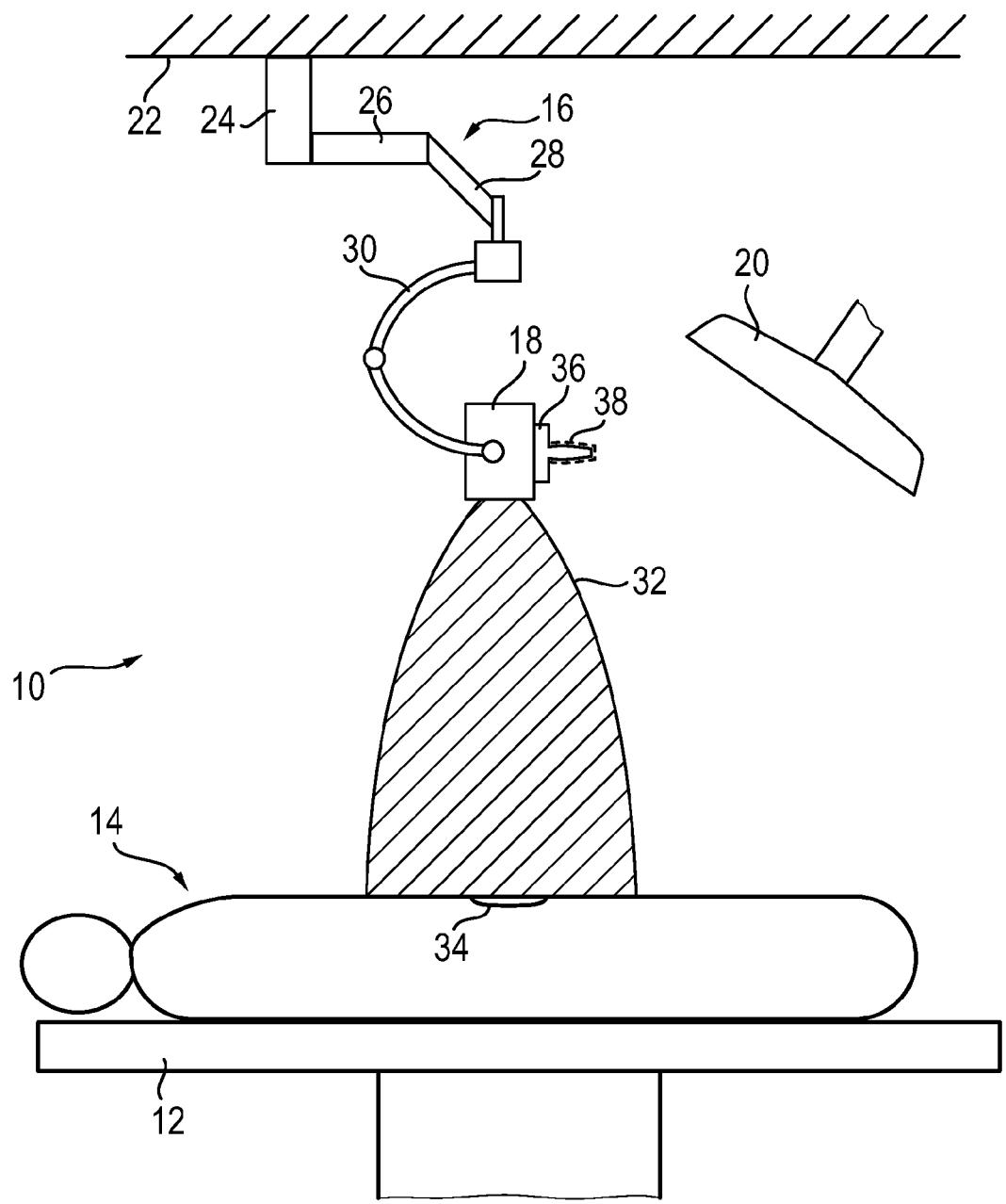
FIG. 1 is a schematic view of an exemplary embodiment of the disinfection device according to the present invention.

Referring to the drawings in particular, FIG. 1 shows a disinfection device 10, which is used in an operating room for the disinfecting wound treatment of a patient 14 lying on an operating table 12. The disinfection device 10 is held movably via a suspension 16 on a ceiling 20. Suspension 16 comprises a central axis 24, an extension arm 26, a spring-loaded arm 28 and a universal joint 30, on which housing 18 is held movably. Supply lines, not shown in FIG. 1, which lead into housing 18 and supply the disinfection device 10 with electricity, compressed air, etc., pass through the suspension 16.

As is shown in FIG. 1, the disinfection device 10 generates a gas stream, which leaves housing 18 in the form of a free jet 32 directed towards patient 14, in the manner explained more specifically below. The free jet 32 contains a plasma, which exerts disinfecting action on a wound 34.

A handle 36, on which a sterile cover 38 is seated, is located on an outside of housing 18. The surgical staff can bring the housing 18 held movably on the suspension 16 by means of the handle 36 provided with the cover 38 into a target position in order to direct the free jet 32 towards the wound 34 as desired.

Figure 2:
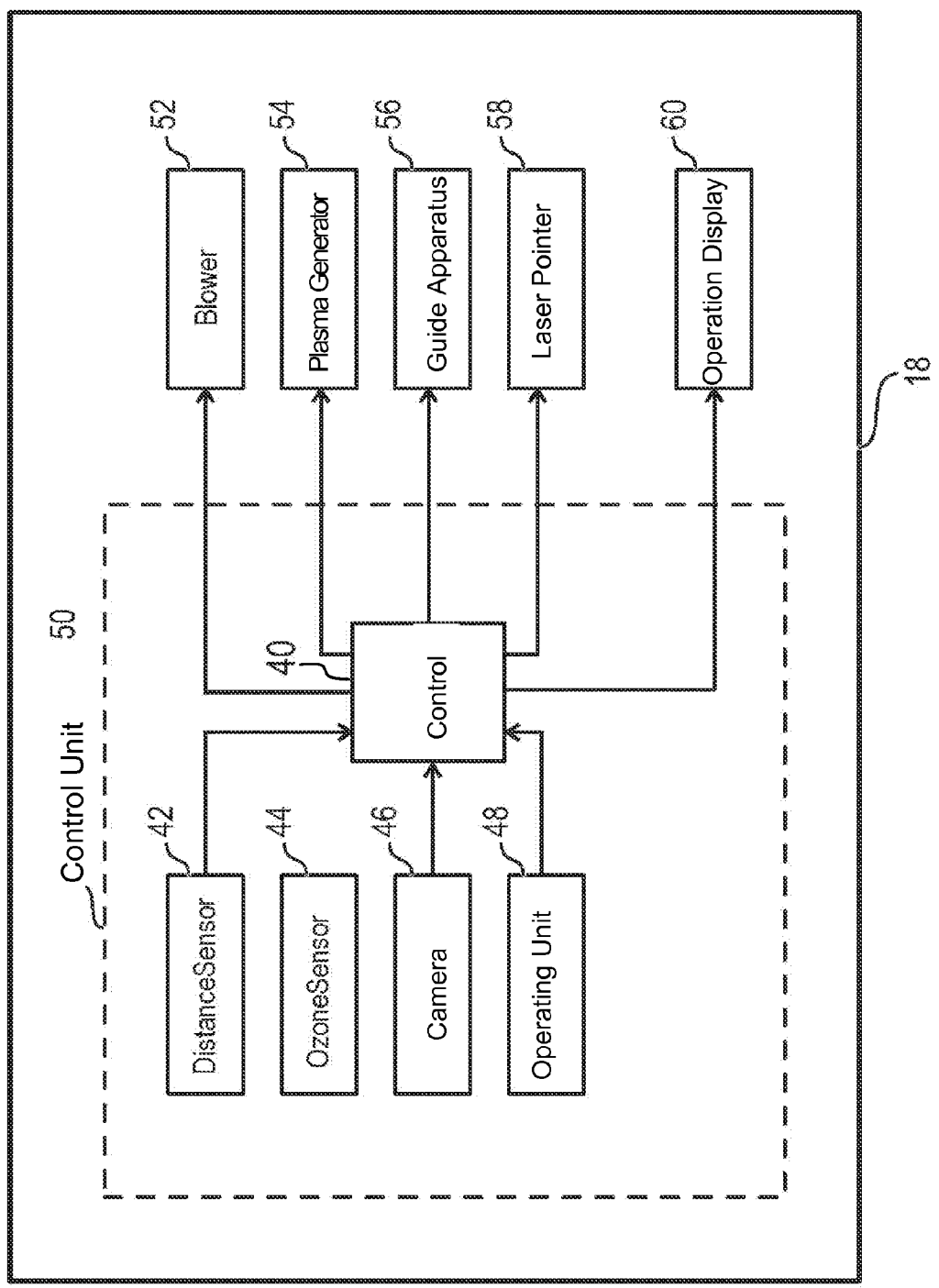
FIG. 2 is a block diagram of a jet control unit and of the components controlled by this.

FIG. 2 shows components of the disinfection device 10, which interact with one another (not shown specifically in FIG. 1), in a block diagram.

The disinfection device 10 has a control 40, which receives signals from a distance sensor 42, an ozone sensor 44, a camera 46 and an operating unit 48. Control 40, distance sensor 42, ozone sensor 44, camera 46 and operating unit 48 form a jet control unit 50.

The distance (space) sensor 42 is arranged, e.g., on a front surface of the housing 18 facing the wound 34 and thus detects the distance between this housing surface and the wound 34. The ozone sensor 44 and camera 46 may also be arranged on this front surface. While the ozone sensor 44 detects the ozone concentration in the room air, the camera 46 generates a picture of the wound 34 being treated, which the surgical staff can view on a monitor, not shown. Camera 46 has, e.g., an autofocus unit, which focuses the camera's optical system onto the wound 34 being treated. An autofocus signal, which is sent by the autofocus unit and corresponds to be wound 34 to be treated (just as the signal sent by the distance sensor 42 as well) is an indicator of the working distance and can be used as an actuating variable.

The operating unit 48, which is likewise arranged on housing 18, is, for example, a keypad, on which the surgical staff can enter certain operating parameters. Handle 36 may also be part of the operating unit 48, e.g., in the form of a bar element, which is coupled with the control unit 40 and is to be rotated by the surgical staff about its longitudinal axis.

The signals, which are received by the control unit 40 from the components 42, 44, 46 and 48, represent actuating variables, by means of which the control unit 40 can control a blower 52, a plasma generator 54, a guide apparatus 56, a laser pointer 58 and an operation display 60.

Thus, blower 52, which is arranged within housing 18 and generates an air stream, can be controlled, for example, as a function of the working distance detected by the distance sensor 42 or the autofocus unit of camera 46, as a function of the ozone concentration detected by the ozone sensor 44 and/or as a function of an operating parameter entered by the surgical staff via the operating unit 48. Such an operating parameter is, e.g., the output with which blower 52 is operated.

The plasma generator 54 arranged within housing 18 generates the plasma having disinfecting action in the air stream, which is delivered by blower 52. The plasma generator 54 can likewise be controlled for this via the signals sent from the components 42, 44, 46 and 48 to the control unit 40.

Guide apparatus 56 has the function of guiding the free jet 32 in the desired manner. One of the signals generated by the components 42, 44, 46 and 48 can again be used as an actuating variable as a function of which the guide apparatus 56 is controlled. Especially the working distance detected by the distance sensor 42 or the autofocus unit of camera 46, on the basis of which, for example, the expansion of the free jet 32 can be set, can be used for this.

Laser pointer 58 is a laser light source, which is arranged on the front surface of the housing 18 facing the wound 34. It is used to generate a light pattern, on the basis of which the surgical staff can visually detect a target area, within which the plasma concentration is high enough to achieve the desired disinfecting action, on the wound area containing the wound 34 in a manner to be explained in more detail below. Laser pointer 58 is actuated as a function of the working distance, which the distance sensor 42 or the autofocus unit of camera 46 detects.

The operation display 60 is used to inform the surgical staff of the operating state of means 10. It is, for example, a light source, which is arranged in the area of the jet discharge opening of housing 18 and is switched on during the free jet generation, which prompts the surgical staff to take action on a corresponding input on the operating unit 48.

Figure 3:
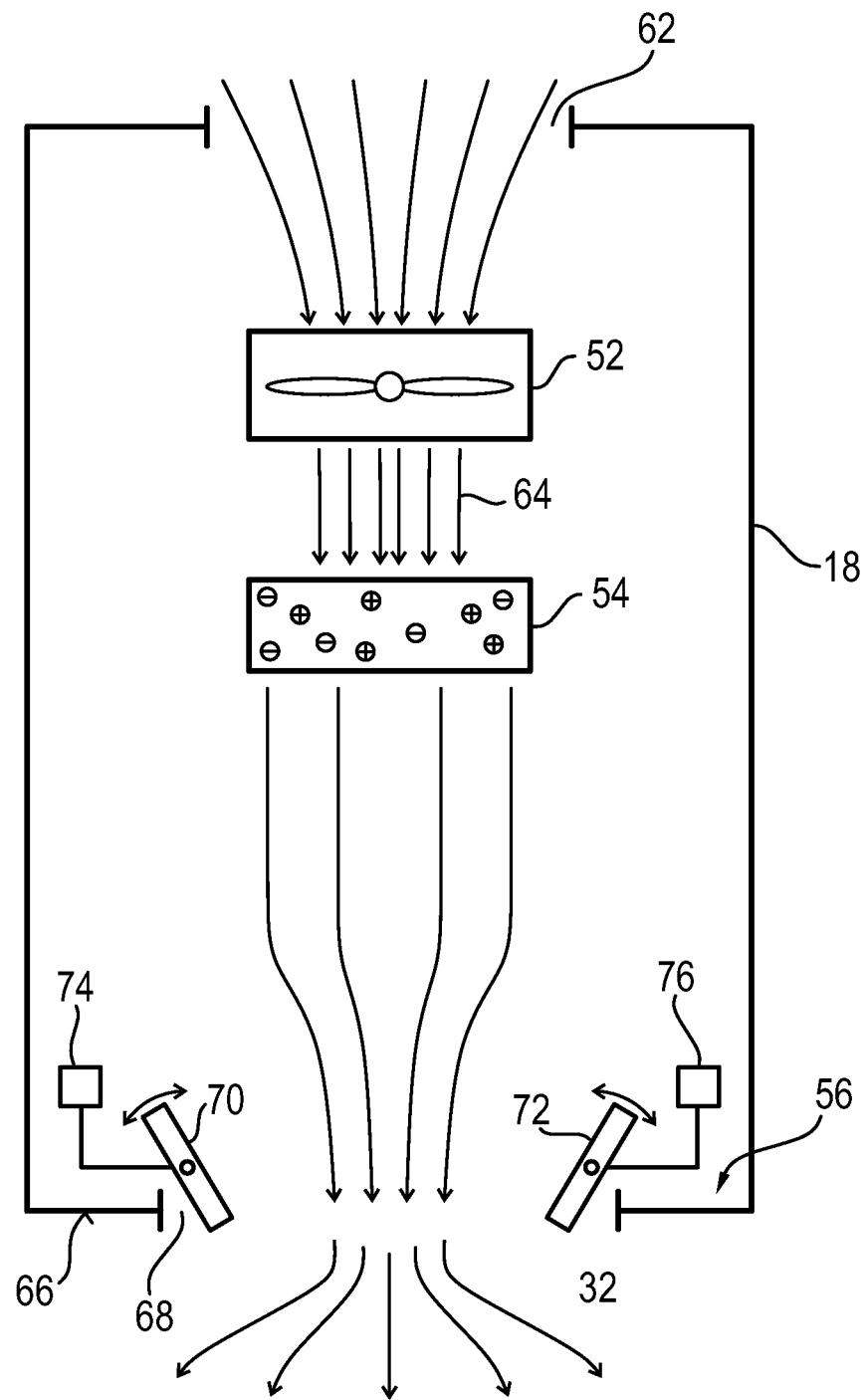
FIG. 3 is a schematic view, in which especially a blower, a plasma generator and a guide apparatus for guiding the free jet are shown.

FIG. 3 is a highly simplified, schematic view, in which the generation and guiding of the free jet 32 are illustrated. FIG. 3 shows only the components that are helpful for understanding.

Blower 52 draws air into the housing 18 via an air inlet opening 62 and thus generates an air stream 64, which is directed towards the plasma generator 54. The air stream 64 flows through the plasma generator 54 and is partially ionized in the process, as a result of which disinfecting plasma is added to the air stream 64. The air stream 64 containing the plasma is then discharged from the housing 18 from an outlet opening 68 formed in the front surface 66 in the form of a free jet 32 into the free environment.

Figure 4:
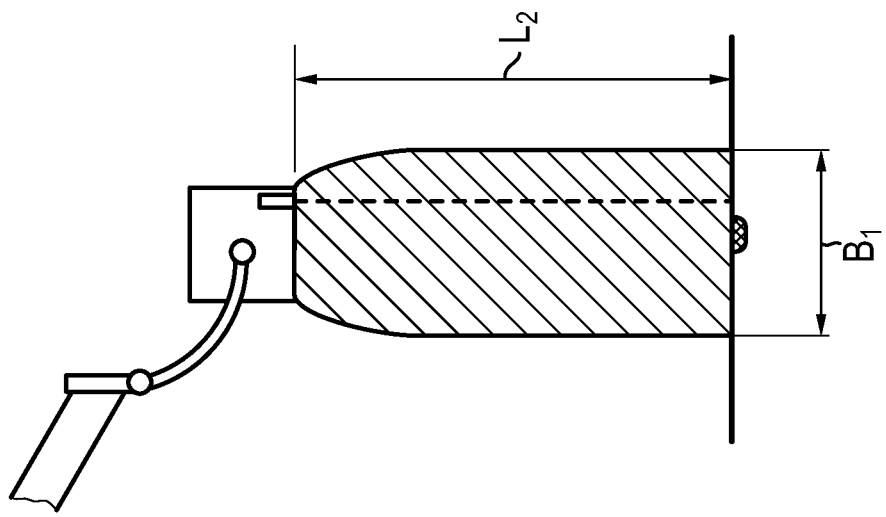
FIG. 4 is a schematic view, in which various orientations of the free jet are shown.
Figure 4:
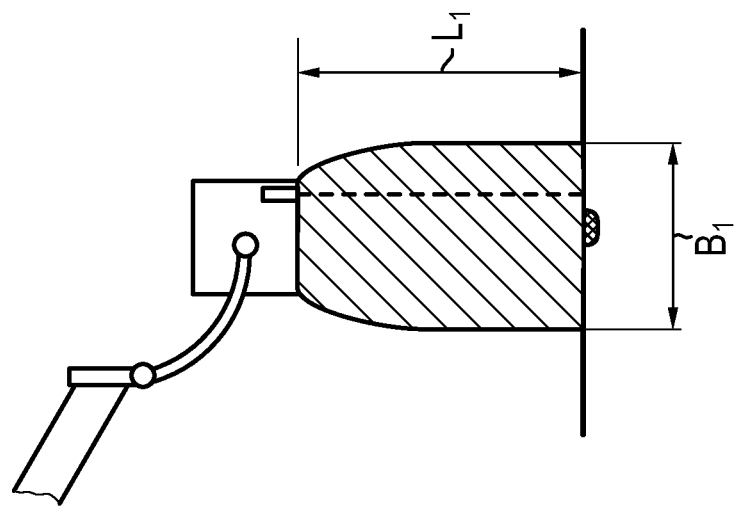

Guide apparatus 56 is formed from a plurality of guide plates 70, 72 with adjustable angles, which are arranged in the area of discharge opening 68. A respective actuator 74 and 76 is associated with each of the guide plates 70, 72. Actuators 74, 76 are controlled by the control unit 40, not shown in FIG. 3, as a function of one or more of the actuating variables that are supplied by the distance sensor 42, ozone sensor 44, camera 46 and/or operating unit 48. The guide apparatus 56 is preferably actuated as a function of the working distance detected by the distance sensor 42 or the autofocus unit of camera 46. If, for example, the working distance is comparatively great, the guide plates 70, 72 are adjusted by means of the actuators 74, 76 such that the cross section of the discharge opening 68, which cross section lets gas pass through, is comparatively small in order to thus correspondingly reduce the expansion of the free jet 32. If, by contrast, the working distance is comparatively short, the discharge opening 68 is correspondingly enlarged by means of a corresponding adjustment of the angles of guide plates 70, 72. This fact is shown in FIG. 4 for two different working distances L1 and L2. The region within the wound area, on which the free jet 32 falls, is more or less equal in both cases.

Figure 5:
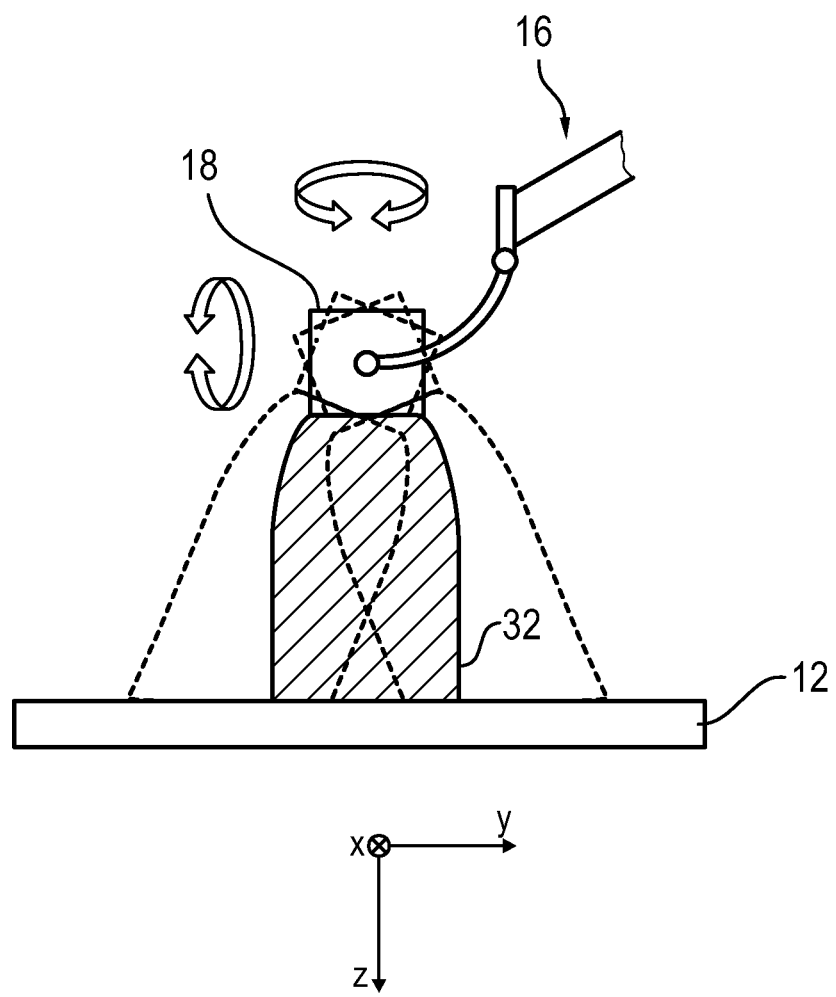
FIG. 5 is a schematic view, which shows various expansions of the free jet for various working distances.

Not only the expansion, but also the direction of discharge of the free jet 32 can be changed by means of the guide apparatus 56. However, such a change can also be brought about in an alternative embodiment merely by pivoting the housing 18 on the suspension 16, as this is illustrated in FIG. 5.

Figure 7:
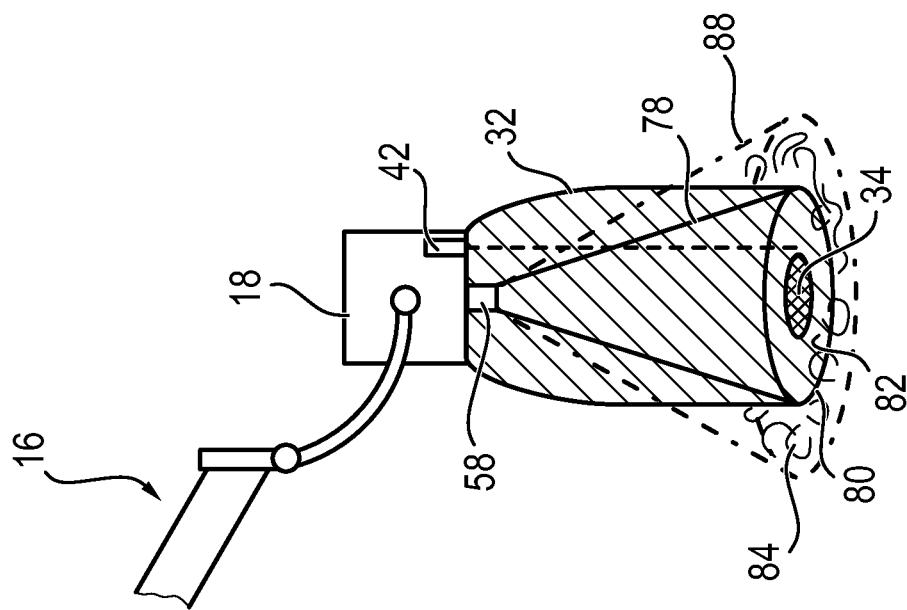
FIG. 7 is a schematic view, which shows a second example of a light pattern generated by the laser pointer.
Figure 6:
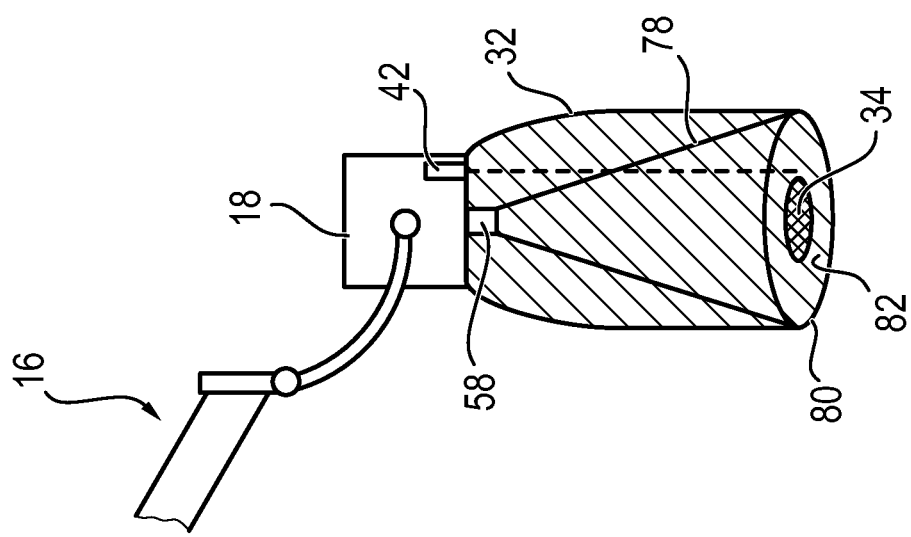
FIG. 6 is a schematic view, which shows a first example of a light pattern generated by a laser pointer.

FIGS. 6 and 7 schematically show two examples of the mode of operation of laser pointer 58.

In FIG. 6, laser pointer 58 draws a circular line 80, which encloses a target area 82, on the wound area containing the wound 34 by means of a laser beam 78 rotating about the central longitudinal axis of housing 18. The size of this target area 82 is set as a function of the working distance detected by distance sensor 42. The control unit 40 shown in FIG. 2 converts for this the working distance sent to it by the distance sensor 42 or the camera 46, optionally taking into account the quantity of plasma generated by plasma generator 52, into an actuating variable, by which the target area 82 is set such that a plasma concentration that is equal to or higher than a desired minimum effective concentration can be assumed within the target area. The surgical staff can thus visually detect in a simple manner the region of the wound area in which the plasma has disinfecting action.

FIG. 7 shows another example, in which laser pointer 58 draws, in addition to the target area 82, an area 84, which encloses the target area 82 and in which the plasma concentration is lower than the above-mentioned minimum effective concentration, but is higher than a tolerable working concentration. This working concentration sets a limit for the plasma concentration, beginning from which health hazard to the surgical staff cannot be ruled out, at least if this concentration persists over a longer time. Area 84 is defined by a second circular line 86, which is arranged with a greater radius concentrically to the first circular line 80. Circular line 86 is drawn by means of a second laser beam 88, which rotates about the central longitudinal axis of housing 18.

Figure 9:
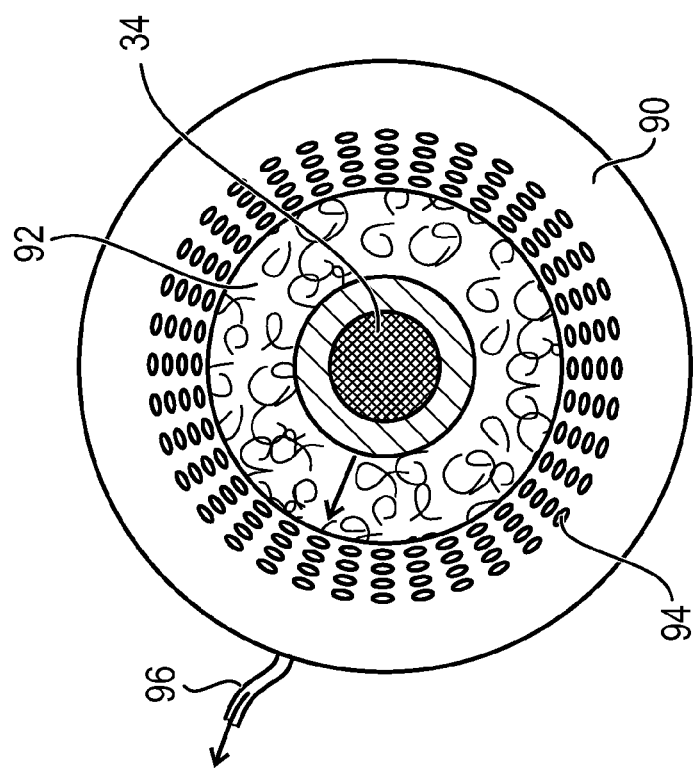
FIG. 9 is a top view of the apron.
Figure 8:
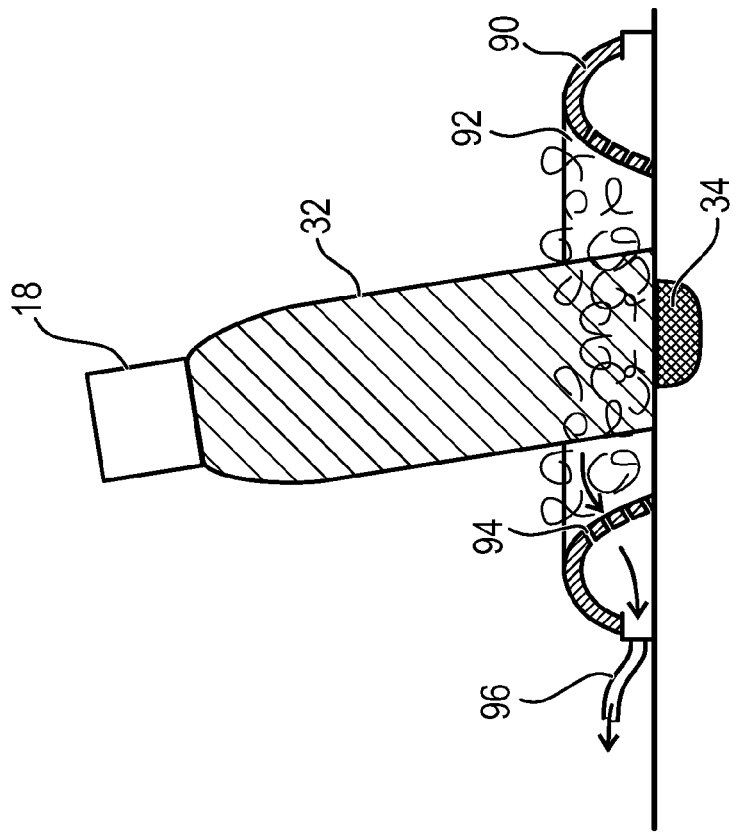
FIG. 8 is a schematic view, in which the use of an apron for locally limiting and exhausting the plasma in the region of a wound area is shown.

FIGS. 8 and 9 show the use of an apron 90, which is used to locally limit the plasma being transported with the free jet 32 in the wound area.

As is shown in the top view according to FIG. 9, apron 90 forms a ring-shaped tube, whose ring opening forms an opening 92 for the wound. Apron 90 is placed on the patient such that the wound 34 to be treated is arranged within the opening 92 for the wound.

Apron 90 has a plurality of suction openings 94 as well as a suction pipe connection 96, which can be connected to a suction device, not shown.

As is illustrated in the side view according to FIG. 8, apron 90 can be used, in cooperation with the suction device, to draw off the gas cloud present in the region of the wound area. Thus, when the suction device is put into operation, the gas cloud containing the plasma is drawn into the apron 90 via the suction openings 94 and disposed off via the suction pipe connection 96. An activated carbon filter, by which the gas drawn off is filtered and thus rendered harmless, may be provided in the suction pipe connection 96.

While specific embodiments of the invention have been shown and described in detail to illustrate the application of the principles of the invention, it will be understood that the invention may be embodied otherwise without departing from such principles.

APPENDIX

LIST OF REFERENCE NUMBERS

| | |
|---|---|
| 10 | Means for disinfecting wound treatment |
| 12 | Operating table |
| 14 | Patient |
| 16 | Suspension |
| 18 | Housing |
| 20 | Operating lamp |
| 22 | Ceiling |
| 24 | Central axis |
| 26 | Extension arm |
| 28 | Spring-loaded arm |
| 30 | Universal joint |
| 32 | Free jet |
| 34 | Wound |
| 36 | Handle |
| 38 | Sterile cover |
| 40 | Control unit |
| 42 | Distance sensor |
| 44 | Ozone sensor |
| 46 | Camera |
| 48 | Operating unit |
| 50 | Jet control unit |
| 52 | Blower |
| 54 | Plasma generator |
| 56 | Guide apparatus |
| 58 | Laser pointer |
| 60 | Operation display |
| 62 | Air entry opening |
| 64 | Air stream |
| 66 | Front wall |
| 68 | Discharge opening |
| 70, 72 | Guide plates |
| 74, 76 | Actuators |
| 78 | Laser beam |
| 80 | Circular line |
| 82 | Target area |
| 84 | Outer area |
| 86 | Circular line |
| 88 | Laser beam |
| 90 | Apron |
| 92 | Opening for wound |
| 94 | Suction openings |
| 96 | Suction pipe connection |

What is claimed is:

1. A device for disinfecting wound treatment, the device comprising:
   a housing;
   a plasma generator arranged in said housing for generating a disinfecting plasma;
   a flow module arranged in said housing for generating a gas stream, which forms a free jet transporting the disinfecting plasma from said housing;
   a guide apparatus for guiding the free jet; and
   a jet control unit controlling said guide apparatus for affecting the free jet in a planned manner by controlling the gas stream generated by said flow module, wherein:
   said guide apparatus has at least one guide element arranged at a gas discharge opening of said housing, said guide element being variably positionable relative to the housing;
   said jet control unit controls said guide apparatus by varying a position of said variably positionable guide element relative to the housing for affecting the free jet in a planned manner by controlling the gas stream generated by said flow module; and
   said jet control unit controls said guide apparatus for varying, with the guide apparatus, at least one of a jet cross section of the free jet being discharged from housing and a direction of discharge, relative to the housing, of the free jet being discharged from the housing.

2. A device in accordance with claim 1, wherein said jet control unit controls said flow module including setting the velocity of the gas stream with said flow module.

3. A device in accordance with claim 1, wherein said jet control unit controls the plasma generator including setting the plasma concentration in the gas stream with said plasma generator.

4. A device in accordance with claim 1, wherein said jet control unit comprises a sensor for detecting an actuating variable and said jet control unit controls the gas stream as a function of said actuating variable.

5. A device for disinfecting wound treatment, the device comprising:
   a housing;
   a plasma generator arranged in said housing for generating a disinfecting plasma;
   a flow module arranged in said housing for generating a gas stream, which forms a free jet transporting the disinfecting plasma from said housing;
   a guide apparatus for guiding the free jet; and
   a jet control unit controlling said guide apparatus for affecting the free jet in a planned manner by controlling the gas stream generated by said flow module, wherein:
   said guide apparatus has at least one variably positionable guide element arranged at a gas discharge opening of said housing;
   said jet control unit controls said guide apparatus by varying a position of said variably positionable guide element for affecting the free jet in a planned manner by controlling the gas stream generated by said flow module
   said jet control unit comprises a sensor for detecting an actuating variable and said jet control unit controls the gas stream as a function of said actuating variable; and
   said sensor is an ozone sensor, which detects the ozone concentration in the ambient air as an actuating variable.

6. A device in accordance with claim 4, wherein said sensor is a distance sensor, which detects a working distance from a wound area to be treated as an actuating variable.

7. A device in accordance with claim 1, further comprising a light pointer controlled via said jet control unit, said light pointer generating a light pattern on a wound area to be treated, which represents a target area, in which a concentration of the plasma being transported in the free jet is equal to or higher than a desired minimum effective plasma concentration.

8. A device in accordance with claim 7, wherein said light pointer is controlled such that said light pattern generated by said light pointer on the wound area has an inner area representing the target area and an outer area, which surrounds the inner area and which is visually distinguished from the inner area and represents an area in which the concentration of the plasma is lower than the minimum effective plasma concentration and is higher than a tolerable working plasma concentration.

9. A device in accordance with claim 7, wherein said light pointer is a laser light source.

10. A device in accordance with claim 1, wherein said flow module comprises a blower directing the gas stream towards the plasma generator.

11. A device in accordance with claim 1, further comprising a movable ceiling suspension, said housing being arranged on said movable ceiling suspension.

12. A device in accordance with claim 11, further comprising a handle arranged on said housing for manually moving said housing.

13. A device in accordance with claim 11, wherein said handle is part of said jet control device with said jet control device actuatable manually via said handle to control the gas stream.

14. A device in accordance with claim 12, further comprising a sterile cover provided on said handle.

15. A device in accordance with claim 1, further comprising a display device for displaying an operating state.

16. A device in accordance with claim 1, further comprising an apron provided with a hole for the wound for locally limiting the plasma in the region of a wound area.

17. A device in accordance with claim 16, wherein said apron is formed from a ring-shaped tube, which has a plurality of suction openings and a suction pipe connection for connecting a suction device.

18. A device for disinfecting wound treatment, the device comprising:
- a housing with a gas intake opening and a gas outlet opening;
- a flow module operatively connected to said housing for generating a gas stream;
- a plasma generator operatively connected to said housing for generating a disinfecting plasma that is transported by the gas stream;
- a guide apparatus for guiding the gas stream as a free jet discharged from said gas outlet opening and transporting the disinfecting plasma from said housing; and
- a jet control unit controlling said guide apparatus by controlling the gas stream generated by the flow module, the jet control unit controlling a position of the guide apparatus relative to the housing and the guide apparatus acting on the gas stream generated by the flow module, as the gas stream is discharged from the housing for affecting a free jet by varying at least one of a jet cross section of the free jet and a direction of discharge of the free jet, relative to the housing, in a controlled manner.

19. A device for disinfecting wound treatment, the device comprising:
- a housing with a gas intake opening and a gas outlet opening;
- a flow module operatively connected to said housing for generating a gas stream;
- a plasma generator operatively connected to said housing for generating a disinfecting plasma that is transported by the gas stream;
- a guide apparatus for guiding the gas stream as a free jet discharged from said gas outlet opening and transporting the disinfecting plasma, in the free jet, from said housing, said guide apparatus comprising a variably positionable guide element arranged at said gas discharge opening of said housing; and
- a jet control unit configured to:
- control said guide apparatus to act on the gas stream, generated by said flow control module, as said gas stream exits the gas discharge opening as the free jet, by varying a position of said variably positionable guide element relative to the housing to change at least one of a jet cross section of the free jet being discharged from the housing and a direction of discharge, relative to the housing, of the free jet being discharged from the housing to affect the free jet in a planned manner;
- control said flow module including setting the velocity of the gas stream generated by said flow module; and
- control said plasma generator including setting a plasma concentration in the gas stream by setting a quantity of plasma generated by said plasma generator.

\* \* \* \* \*